United States Patent

Nardella et al.

[11] Patent Number: 5,925,040
[45] Date of Patent: Jul. 20, 1999

[54] ELECTROSURGICAL INSTRUMENT HAVING A SEGMENTED ROLLER ELECTRODE

[75] Inventors: Paul C. Nardella, Wareham; Kevin M. Allaire, Mattapoisett; Thomas A. Wrublewski, Sharon, all of Mass.

[73] Assignee: Medical Scientific, Inc., Taunton, Mass.

[21] Appl. No.: 08/878,389

[22] Filed: Jun. 18, 1997

[51] Int. Cl.$^6$ .................................................. A61B 17/39
[52] U.S. Cl. ............................... 606/41; 606/46; 606/48; 606/49; 606/50
[58] Field of Search ................. 606/41, 45, 46, 606/48, 49, 50; 601/147, 20

[56] References Cited

U.S. PATENT DOCUMENTS

| | | | |
|---|---|---|---|
| Re. 33,925 | 5/1992 | Bales et al. | 606/48 |
| 4,116,198 | 9/1978 | Roos | 128/303.15 |
| 4,311,143 | 1/1982 | Komiya | 128/303.15 |
| 4,362,160 | 12/1982 | Hiltebrandt | 128/303.15 |
| 4,842,578 | 6/1989 | Johnson et al. | 604/22 |
| 4,920,978 | 5/1990 | Colvin | 128/784 |
| 5,158,087 | 10/1992 | Gatzke | 128/662.03 |
| 5,290,282 | 3/1994 | Casscells | 606/29 |
| 5,312,327 | 5/1994 | Bales et al. | 604/21 |
| 5,342,358 | 8/1994 | Daikuzono | 606/45 |
| 5,376,087 | 12/1994 | Haber et al. | 606/27 |
| 5,383,876 | 1/1995 | Nardella | 606/49 |
| 5,395,363 | 3/1995 | Billings et al. | 606/48 |
| 5,411,514 | 5/1995 | Fucci et al. | 606/180 |
| 5,423,813 | 6/1995 | Kaiser et al. | 606/46 |
| 5,484,435 | 1/1996 | Fleenor et al. | 606/46 |
| 5,486,173 | 1/1996 | Vancaillie | 606/45 |
| 5,492,527 | 2/1996 | Glowa et al. | 604/22 |
| 5,549,605 | 8/1996 | Hahnen | 606/46 |
| 5,569,244 | 10/1996 | Hahnen | 606/46 |
| 5,634,924 | 6/1997 | Turkel et al. | 606/46 |
| 5,759,183 | 6/1998 | VanDusseldorp | 606/50 |

*Primary Examiner*—Lee Cohen
*Attorney, Agent, or Firm*—Nutter, McClennen & Fish, LLP

[57] ABSTRACT

An electrosurgical instrument includes a roller electrode segmented into conductive and non-conductive portions. When the electrode is rolled over a treatment site, the region of the electrode that contacts the site receives current from an energy source and the non-contacting region of the electrode is isolated from the energy source. The electrode is well suited for use in an isotonic fluid environment, without resulting in significant current dissipation since the non-contacting portion is isolated from the energy source. The roller electrode has a substantially cylindrical shape and is rotatable about a longitudinal axis along which a bore extends. A conductor carrying current from the energy source is disposed through the bore such that, when the electrode is urged against a treatment site, the conductor delivers current to the contacting region of the roller electrode and is isolated from the non-contacting region. Various designs of the segmented roller electrode, as well as both monopolar and bipolar embodiments, are described.

22 Claims, 6 Drawing Sheets

ELECTROSURGICAL INSTRUMENT HAVING A SEGMENTED ROLLER ELECTRODE

CROSS REFERENCE TO RELATED APPLICATION

Not Applicable.

STATEMENTS REGARDING FEDERALLY SPONSORED RESEARCH

Not Applicable.

BACKGROUND OF THE INVENTION

Electrosurgical devices utilize electrical current, such as radio frequency (RF) energy, to cut and cauterize tissue. Instruments for performing electrosurgery generally include an energy source, or generator, an active electrode for delivering electrical energy to tissue to be treated, a return electrode to complete the electrical circuit and conductors for coupling the energy source to the active and return electrodes.

Various types of open and closed surgical procedures utilize electrosurgical devices. Closed surgical procedures include arthroscopic, endoscopic, hysteroscopic, urologic, resectoscopic and laparoscopic procedures. For example, a hysteroscope is used in a closed surgical procedure for treatment of various conditions within a woman's uterine cavity. Typical uses of hysteroscopes include fibroid removal, intrauterine adhesion removal, endometrial ablation and correction of abnormal uterine bleeding.

The terms monopolar or bipolar can be used to characterize certain electrosurgical instruments. A monopolar electrosurgical instrument includes an active electrode for cutting tissue and a remotely located return electrode for providing a return current path. Bipolar instruments, on the other hand, are generally characterized by the return electrode being located in close proximity to the active electrode. The bipolar arrangement serves to restrict the area of current flow between the two electrodes, which may be desirable in certain applications, particularly where tissue damage is a concern.

Some surgical procedures, such as arthroscopic and hysteroscopic procedures, require distension of the surgical area in order to increase visibility at the treatment site or to minimize space constraints. In some instances, the surgical area is distended using a fluid.

An electrolyte-free (i.e., hypotonic) distension fluid is typically used in such procedures in order to prevent the electrical current delivered by the active electrode from dissipating to an ineffective level. However, absorption of excessive quantities of hypotonic solution into a patient's bloodstream can alter the patient's electrolyte levels and potentially result in dangerous conditions, including cardiac arrhythmia, brain swelling and even death. The risk of these dangers may cause the surgeon to terminate the procedure before completion. Furthermore, hypotonic solutions are expensive as compared to isotonic solutions.

The active electrode of electrosurgical instruments can take various forms. Exemplary active electrodes include conductive blades, conductive loops and conductive rollable cylinders (i.e., "rollers"). With conductive loops, the area of tissue contact is limited, thus requiring significant precision in manipulation of the electrode. While a roller provides a broader tissue contact area, which is advantageous in certain applications, its use has conventionally been limited to hypotonic fluid environments, in order to prevent undesirable dissipation of the current delivered by the conductive roller. This is because a significant conductive surface area of the roller which does not contact the tissue would conduct current to surrounding isotonic fluid and away from the treatment site.

SUMMARY OF THE INVENTION

The invention is directed to a segmented roller electrode which, even when used in a monopolar electrosurgical instrument, is advantageously suitable for use in an isotonic fluid environment. The roller electrode has a substantially cylindrical shape and is rotatable about a longitudinal axis such that a region of the electrode that contacts the treatment site (i.e., the "contacting region") receives current from an energy source for delivery to the treatment site and the region of the electrode that does not contact the treatment site (i.e., the "non-contacting region") is isolated from the energy source. In this way, the current carrying surface area of the roller electrode in contact with the surrounding isotonic solution is reduced, thereby concomitantly reducing current dissipation via the fluid.

In one embodiment, the electrosurgical instrument includes an instrument body having a proximal portion for user handling and a distal portion from which the roller electrode extends. The roller electrode has a bore extending longitudinally therethrough, and the instrument further includes a conductor for coupling the energy source to the electrode. More particularly, the conductor extends through the bore so as to deliver current to the contacting region of the electrode and to be isolated from the non-contacting region.

More particularly, the roller electrode is segmented into at least one conductive portion extending from the bore to an outer surface of the electrode and at least one non-conductive portion. In embodiments in which the roller includes two or more conductive portions, such portions are spaced by non-conductive portions. The conductive portions may be angularly spaced around the circumference of the roller electrode and/or longitudinally spaced along the length of the roller. Since only the tissue-contacting region of the roller receives electrical energy, energy dissipation via the isotonic fluid is minimized, even if the non-tissue-contacting region includes one or more conductive portions.

Various designs of the roller electrode are described. In some embodiments, the conductive portions extend longitudinally along at least a portion of the roller electrode. Illustrative of these embodiments are conductive portions having a substantially pie-shaped or semi-circular cross-section.

Alternative embodiments, in which the conductive portions do not extend longitudinally along the roller electrode, are conducive to a drilling procedure for forming the conductive portions. More particularly, holes of various shapes are drilled between the outer surface of the cylindrical roller and the longitudinal bore in order to define the conductive portions which are thereafter filled with a conductive material, such as molten metal. Such conductive portions may be substantially cylindrical (i.e., "plug-shaped") or may be shaped to increase the conductive surface area of the roller electrode by tapering the diameter of the holes towards the bore, such as in the form of cone or pyramid shapes.

Both monopolar and bipolar instruments utilizing the segmented roller electrode are described. In the monopolar embodiments, a return electrode, such as a ground pad, is provided for remote contact with the patient relative to the roller electrode located at the treatment site. In the bipolar embodiments, the roller electrode comprises both the active and return electrodes. More particularly, in one such device, the active and return electrodes are provided by conductive portions of the roller electrode which are angularly spaced from one another around the circumference of the electrode. In an alternate bipolar embodiment, the active and return electrodes are provided by conductive portions of the roller electrode which are laterally spaced from one another along the length of the electrode.

DETAILED DESCRIPTION OF THE INVENTION

Figure 1:
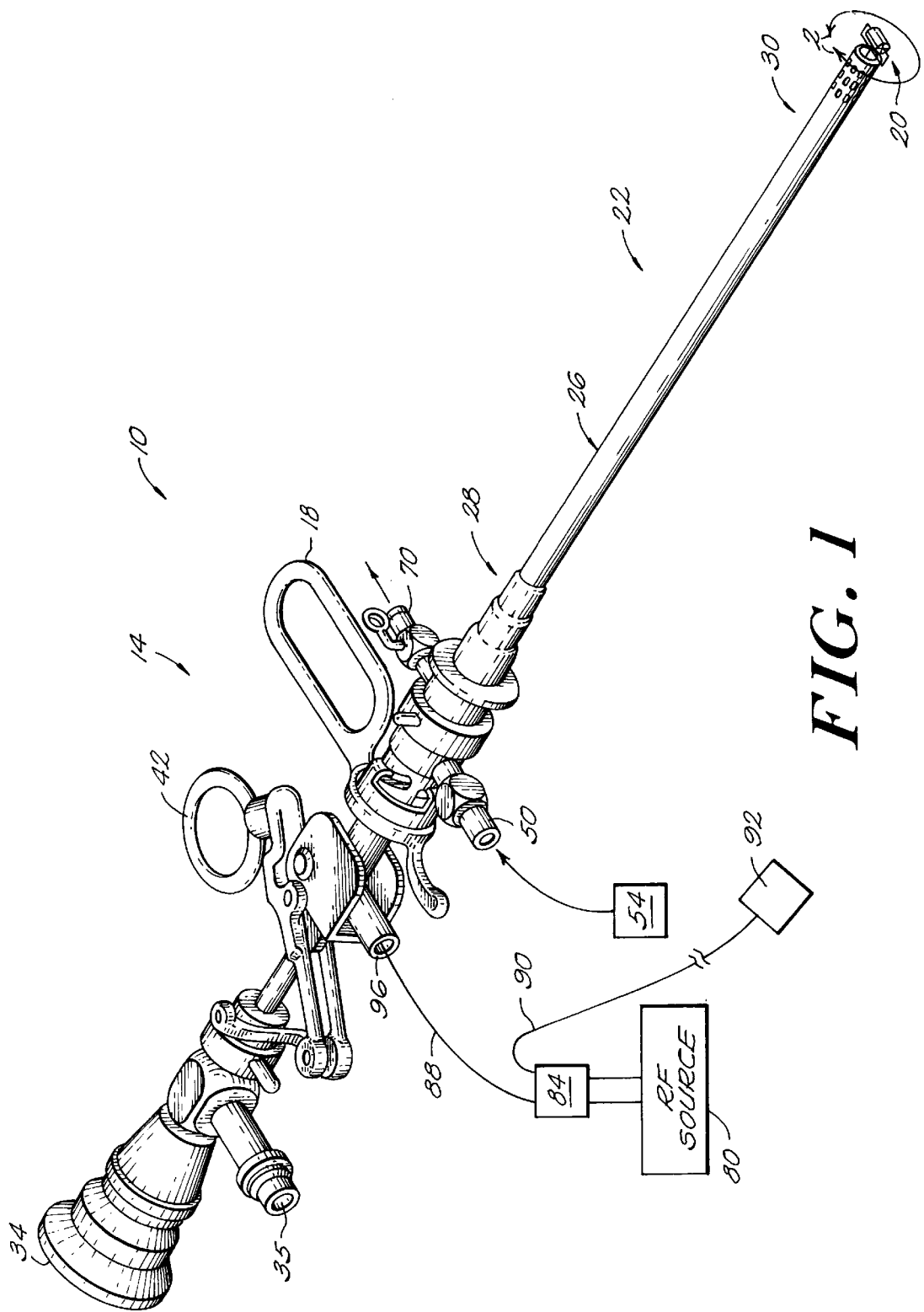
FIG. 1 shows a perspective view of a monopolar electrosurgical instrument having a segmented roller electrode according to the invention.
Figure 2:
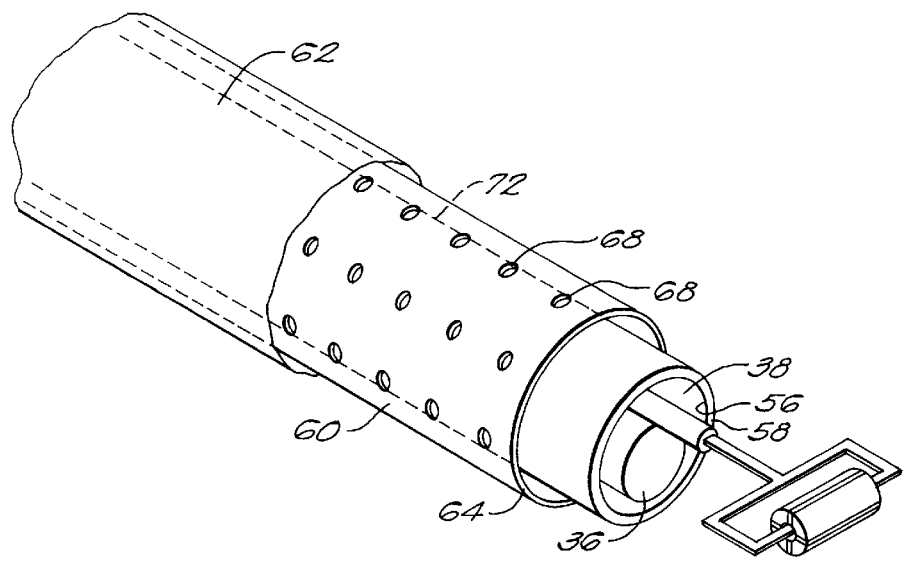
FIG. 2 is an enlarged view of the distal end of the electrosurgical instrument of FIG. 1.

Referring to FIGS. 1 and 2, in which like reference numbers are used to indicate the same elements, an electrosurgical instrument 10 includes an active electrode 20, in the form of a segmented roller, for delivering electrical current to a treatment site of a patient. The instrument is suitable for insertion into the patient in accordance with closed surgery (e.g., arthroscopic, endoscopic, hysteroscopic, urologic, resectoscopic and laproscopic procedures) or open surgery. The illustrative instrument 10 is a hysteroscope in which the roller electrode 20 is intended for insertion into the uterine cavity of a female patient for treatment of various conditions. It will be appreciated however that various types of electrosurgical instruments can be used for other procedures while utilizing and achieving the advantages of the segmented roller electrode described herein.

The instrument 10 includes a proximal portion 14, including a handle 18 for user handling of the instrument in order to guide the electrode 20 into contact with the treatment site and a distal, or forward portion 22. The forward portion 22 includes an elongated probe 26 having a proximal end 28 adjacent to the handle 18 and a distal end 30 from which the roller electrode 20 retractably extends. The electrode 20 is capable of being moved along the longitudinal axis of the probe 26 so as to extend through an aperture 38 at the distal end 30 of the probe 26 to contact tissue or to be retracted into the end 30 of the probe 26 through the aperture 38. An actuator 42 permits retraction and extension of the electrode 20 via a mechanical coupling within the probe 26.

An optical path within the instrument 10 extends between an eye piece 34 at the rearward portion 14 and a lens 36 at the distal end 30 of the probe 26 (FIG. 2). The optical path permits the surgeon to view the treatment site. To further facilitate visualization of the treatment site, a light delivery port 35 permits light to be introduced into the optical path.

The electrosurgical instrument 10 is capable of delivering fluid to and collecting fluid from the treatment site. To this end, the instrument 10 includes a fluid input port 50 which is adapted for coupling to an external fluid source 54. The fluid thus introduced into the instrument 10 is directed toward the distal end 30 of the probe 26 via a first, inner fluid channel 56 (FIG. 2), where the fluid exits the instrument aperture 38. More particularly, the first fluid channel 56 is defined by an inner sheath 58. A second, outer fluid channel 60 between an outer sheath 64 of the probe 26 and the inner sheath 58 serves to collect fluid from the treatment area. To this end, a fluid intake, such as apertures 68 through the outer sheath 64, permit fluid collection. Fluid from the treatment area flows through the second fluid channel 60 toward the proximal end 28 of the probe 26, where the fluid exits the instrument through a fluid output port 70.

With the use of the segmented roller electrode 20 described herein, the fluid introduced to the treatment site can be isotonic fluid, without sacrificing the effectiveness of the device due to current dissipation. That is, the roller electrode 20 is segmented into at least one conductive portion and at least one non-conductive portion and electrical energy is coupled to the electrode 20 in such a way that minimal current dissipation occurs through the isotonic fluid. The roller electrode 20 is described in detail below. Suffice it to say that, in use, current is coupled to a tissue-contacting region of the electrode and is isolated from the non-tissue-contacting region. With this arrangement, regardless of whether the non-tissue-contacting region comprises one or more conductive portions, this region of the electrode does not carry significant current which would otherwise readily flow into the isotonic fluid.

Illustrative isotonic fluid suitable for use with the electrosurgical instrument 10 includes saline and Ringer's lactate. More generally however, the isotonic fluid used with the instrument 10 has an osmolarity of about 280 milliosmols per liter, and preferably in the range of about 260 to 295 milliosmols per liter.

An energy source 80, such as a source of radio frequency (RF) energy, provides electrical energy for delivery by the roller electrode 20 to the treatment site. More particularly, a control device 84 coupled between the energy source 80 and the instrument 10 permits conventional control of alternating current provided by the source 80, including the ability to turn the energy source on an off as a function of the position of the electrode 20 relative to the treatment site. Conductors 88 and 90 carry current from and to the energy source, respectively, and may be referred to as an active conductor 88 and a return conductor 90.

The illustrative instrument 10 of FIG. 1 is a monopolar device, with the return conductor 90 being coupled to a return electrode in the form of a ground pad 92 which is suitable for attachment to a patient's skin. In particular, in monopolar devices, it is contemplated that the return electrode 92 contacts the patient's body at a remote location relative to the treatment site at which the active electrode 20 is located. The active conductor 88 is coupled to the active roller electrode 20 through an electrical path within the probe 26.

In another embodiment, at least a portion of the outer sheath and/or inner sheath can form a return electrode for the device. As shown in FIG. 2, the outer sheath 64 can have a coated portion 62 that is electrically insulated by the coating material and an exposed return electrode portion 72. The return electrode portion can be formed as desired to obtain a desired amount of surface area for the return electrode of the device. This arrangement eliminates or supplements a return electrode in contact with the patient's body.

Figure 11:
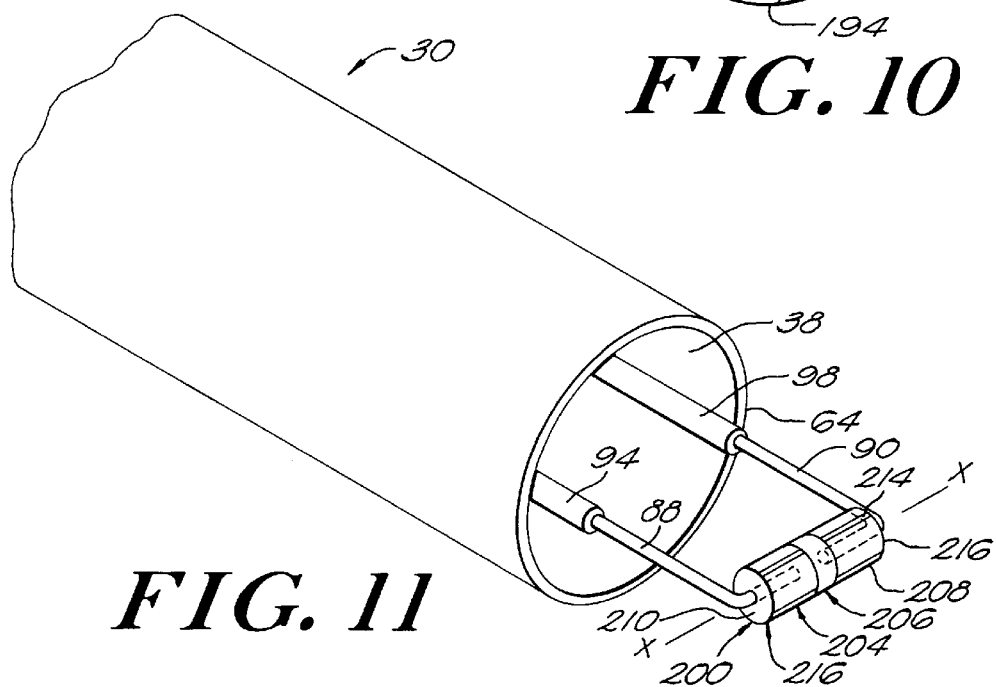
FIG. 11 is a perspective view of the distal end of an electrosurgical instrument having a bipolar segmented roller electrode according to the invention.
Figure 12:
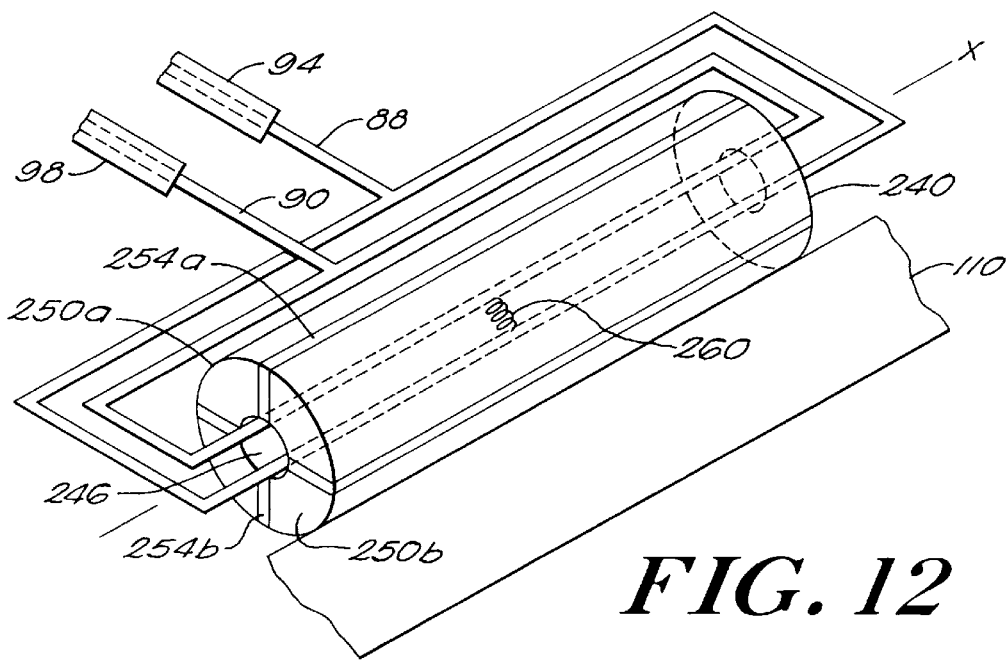
FIG. 12 is a perspective view of an alternate bipolar segmented roller electrode according to the invention.

The segmented roller electrode 20 is particularly advantageous for use with monopolar devices since the segmented roller electrode minimizes problems associated with current dissipation into the surrounding isotonic fluid resulting from the significant distance between the active and return electrodes. However, the segmented roller electrode is likewise advantageous for use with bipolar electrosurgical instruments and instruments in which a portion of a sheath 64 (FIG. 2) provides a return electrode in order to achieve the same advantages. That is, any current dissipation into the surrounding isotonic fluid is likewise minimized by the segmented roller electrode, albeit such dissipation generally presents less of a performance degradation in bipolar instruments due to the proximity of the active and return electrodes. Two embodiments of bipolar segmented roller electrodes are shown in FIGS. 11 and 12. Use of the bipolar electrodes requires the instrument 10 to be modified only in that the return conductor 90, along with the active conductor 88, enters the instrument through the port 96 for coupling to the roller electrode.

Figure 3:
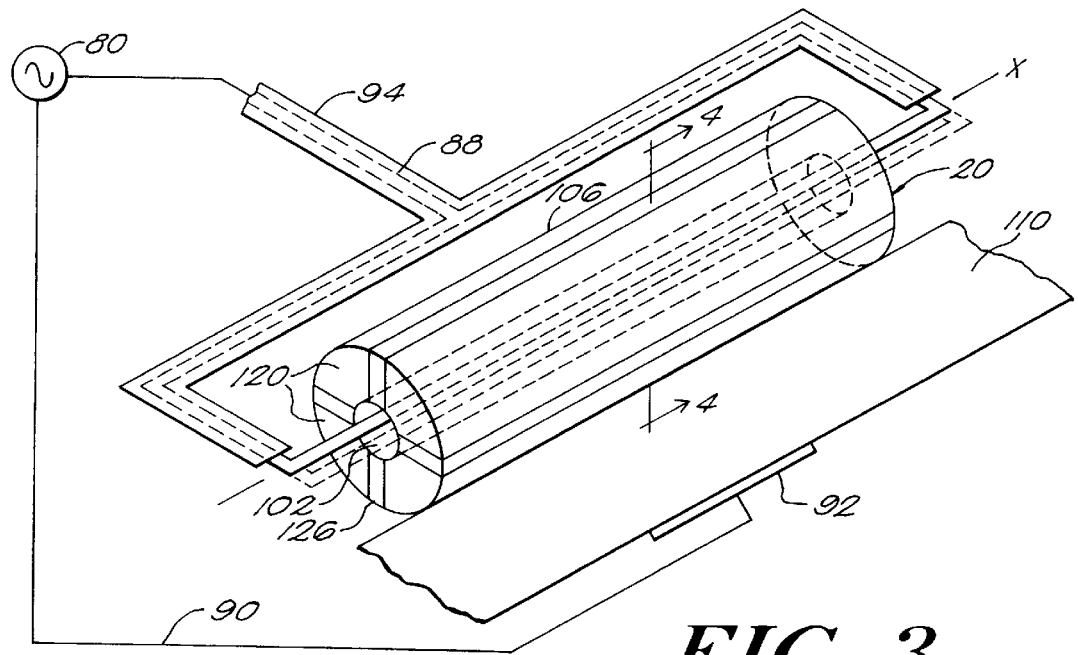
FIG. 3 is an enlarged view of the segmented roller electrode of the electrosurgical instrument of FIG. 1.
Figure 4:
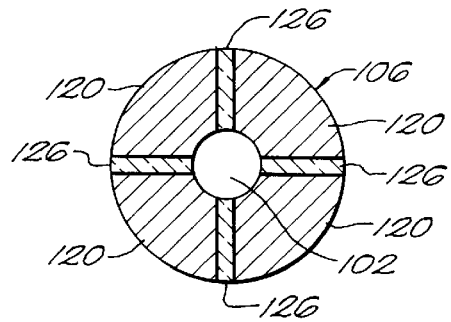
FIG. 4 is a cross-sectional view of the segmented roller electrode of FIG. 3.

Referring also to FIGS. 3 and 4, in which like reference numbers are used to indicate the same elements, an enlarged view of the segmented roller electrode 20 is shown without the probe 26. The segmented electrode 20 is shown in contact with tissue 110 to be treated. Also shown in FIG. 3 are the energy source 80, the active conductor 88, the return conductor 90 and a return electrode 92. Since the exemplary segmented roller electrode 20 is used with a monopolar instrument 10 (FIG. 1), the return electrode 92 is disposed at a location on the patient remote from the treatment site.

The roller electrode 20 has a substantially cylindrical shape and is adapted for rotating about a longitudinal axis X. Rotation of the electrode 20 in use causes the electrode to "roll" over the treatment site such that, at any given time, a region of the roller (i.e., the tissue-contacting or contacting region) contacts the adjacent tissue and another region of the roller (i.e., the non-tissue-contacting or non-contacting region) is spaced from and does not contact the tissue (i.e., is electrically insulated from the tissue).

A bore 102 extends along the longitudinal axis X of the roller electrode 20 and the active conductor 88 extends through the bore 102, as shown. It is contemplated that portions of the conductor 88 are covered with an insulator 94, particularly portions disposed within the probe 26. Conductor 88 extends through the insulator 94 to provide a non-insulated portion for extending through the bore 102. The conductor 88 is moveable relative to the roller such that, when the electrode 20 is urged against a surface such as tissue 110, the roller electrode 20 deflects away from the tissue 110 until the conductor 88 contacts the portion of the bore 102 closest to the tissue 110, as shown in phantom in FIG. 3. Thus, the conductor 88 contacts the tissue-contacting region of the roller electrode 20 and does not contact the non-tissue-contacting region. The control unit 84 may be used to prevent the conductor 88 from delivering current to conductive portions of the electrode prior to the electrode contacting the treatment site by activating the energy source 80 after the electrode is in contact with the treatment site.

It will be appreciated that various mechanical and electrical coupling schemes for coupling the conductor 88 to the electrode 20 such that the conductor is electrically coupled only to the tissue-contacting region are possible. For example, the conductor 88 may extend through only a portion of the bore and additional portions of the conductor may be insulated.

The roller electrode 20 is segmented in the sense that the electrode includes at least one conductive portion 120 and at least one non-conductive portion 126, with conductive portions being separated by non-conductive portions. Each of the conductive portions 120 extends between the bore 102 and the outer surface 106 of the electrode. With this arrangement, when the conductor 88 contacts the tissue-contacting region of the electrode 20, the non-tissue-contacting region of the electrode 20 is isolated from the active terminal of the energy source, even if the non-tissue-contacting region includes one or more conductive portions.

In the embodiment of FIGS. 3 and 4, each of the conductive portions 120 has a substantially wedge, or pie-shaped cross-section and extends between the bore 102 and the outer surface 106 of the electrode. Further, both the conductive portions 120 and the non-conductive portions 126 extend longitudinally along the roller electrode. The embodiments described herein illustrate various ways by which the roller electrode 20 can be segmented into conductive and non-conductive portions. It will be appreciated by those of skill in the art, however, that various other designs are possible and thus, the embodiments described herein are illustrative only. It will be further appreciated that the dimensions of conductive and non-conductive portions are likewise illustrative only.

Various materials are suitable for providing both the conductive and non-conductive portions, depending on factors such as the type of instrument, cost and the manufacturing process by which the roller electrode is fabricated. As examples, the conductive portions may comprise a metal, such as tungsten, stainless steel, gold, platinum and titanium, and the non-conductive portions may comprise a heat stable, biologically compatible material, such as ceramics (e.g., glass, aluminum-silicate, alumina or boron), non-conductive epoxy, ceramic adhesive or other non-conductive polymers such as Teflon, Kynar and Kevlar.

The segmented roller electrode 20 can be manufactured in various ways. As will become apparent, different embodiments of the segmented roller electrode are conducive to different manufacturing techniques. As one example, individual pie-shaped conductive regions 120 can be machined from a metal extrusion and assembled together to form the substantially cylindrical electrode 20 with non-conductive epoxy or ceramic adhesive which provides non-conductive portions 126.

Figure 5:
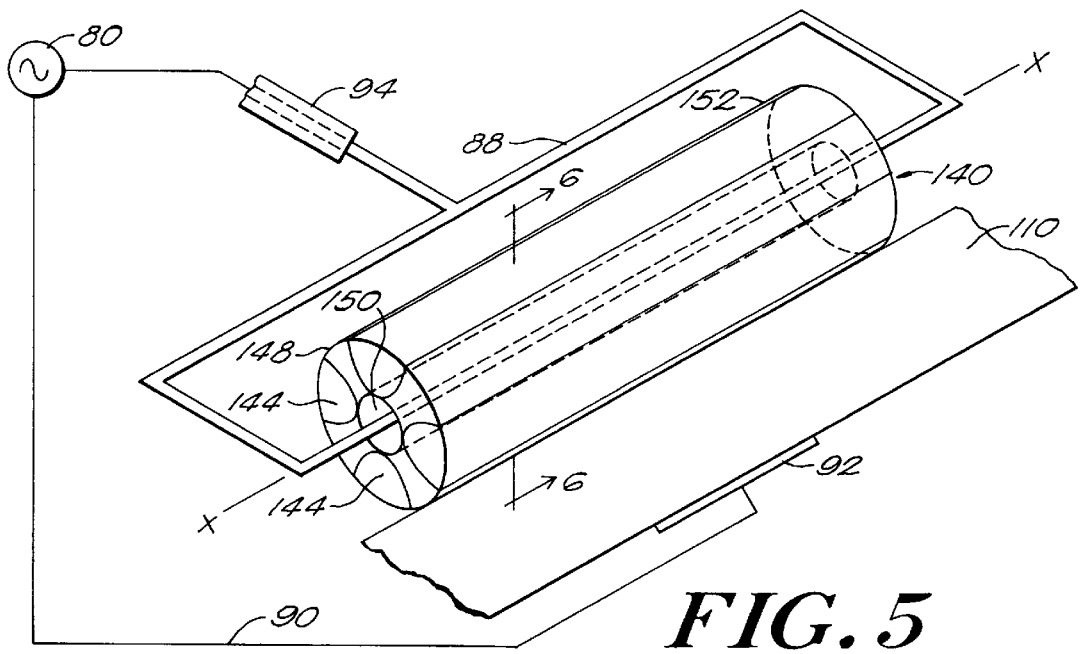
FIG. 5 is a perspective view of a segmented roller electrode according to an alternate embodiment of the invention.
Figure 6:
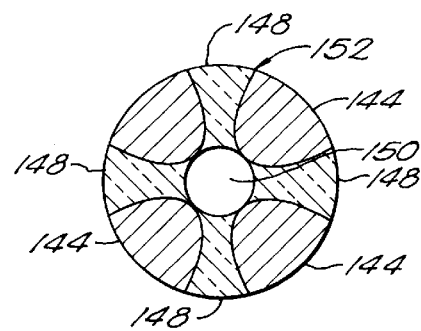
FIG. 6 is a cross-sectional view of the segmented roller electrode of FIG. 5.

Referring also to FIGS. 5 and 6, in which like reference numbers are used to indicate the same elements, an alternate segmented roller electrode 140 for use with the monopolar instrument 10 of FIG. 1 in the treatment of tissue 110 is shown. The electrode 140 receives current from the energy source 80 via the active conductor 88 and a return current path back to the energy source 80 is provided by the remotely located return electrode 92 and the return conductor 90.

Electrode 140, like electrode 20 of FIGS. 3 and 4, is substantially cylindrically shaped and is adapted for rotating about a longitudinal axis X along which a bore 150 extends. The electrode 140 includes conductive regions 144 and non-conductive regions 148, with the conductive regions extending between the bore 150 and the outer surface 152 of the electrode. Like the arrangement of roller electrode 20, the conductive portions 144 and non-conductive portions 148 of the electrode 140 extend longitudinally along the electrode, as shown.

Electrode 140 is similar to electrode 20 also in the arrangement of alternating conductive and non-conductive portions around the circumference of the cylindrical electrode. However, the shape of the conductive portions 144 is somewhat different than the pie-shaped portions 120. In particular, the conductive portions 144 have a substantially semi-circular cross-section, as is evident from FIG. 6.

One way of manufacturing electrode 140 is by drilling the semi-circular portions 144 from a cylindrical insulative extrusion, such as ceramic. Thereafter, the semi-circular portions 144 can be filled with a conductive material, such as molten metal with the use of a cylindrical mold around the roller electrode. Once the metal cools, the bore 150 can be drilled to provide the structure shown. Alternatively, the bore 150 may be drilled at the same time as portions 144 and a mandrel used to prevent the molten metal from entering the bore.

Figure 8:
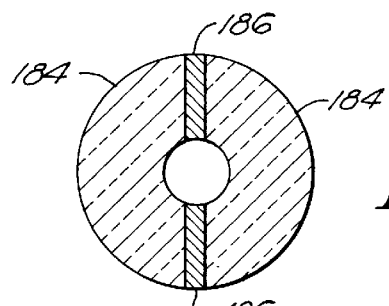
FIG. 8 is a cross-sectional view of the segmented roller electrode of FIG. 7.
Figure 7:
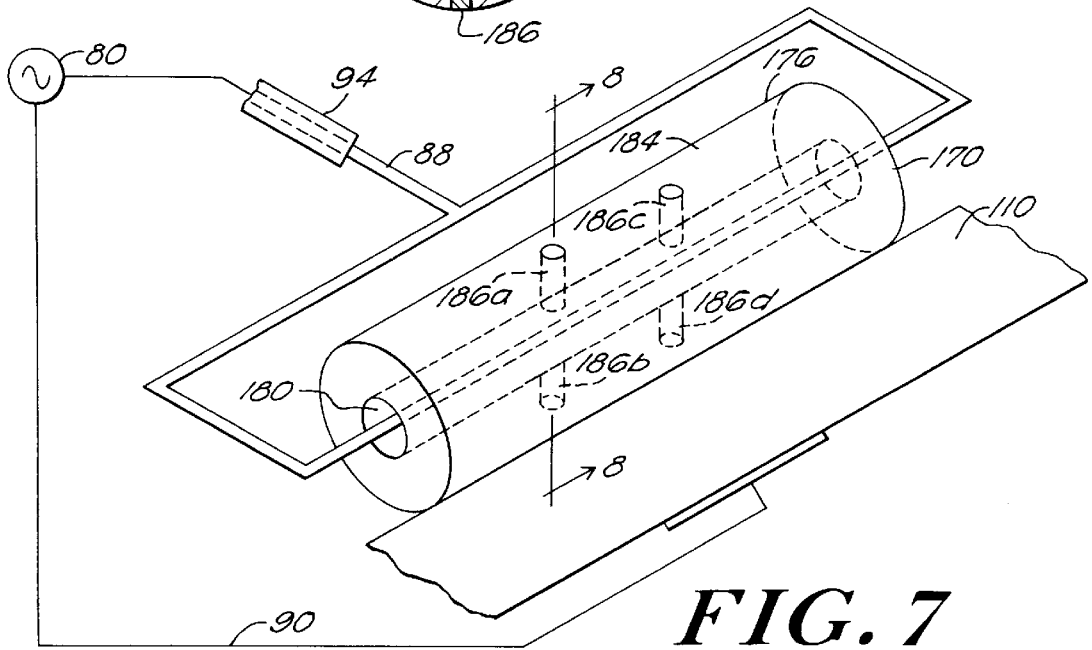
FIG. 7 is a perspective view of a segmented roller electrode according to another alternate embodiment of the invention.

Referring also to FIGS. 7 and 8, where like numbers refer to like elements, an alternate segmented roller electrode 170 is shown with the active conductor 88 extending through a bore 180 along longitudinal axis X. The roller electrode 170 is rotatable about the axis X so as to "roll" over the treatment site 110 of a patient.

The electrode 170 includes conductive portions 186 and non-conductive portions 184, with conductive portions 186 extending from the bore 180 to an outer surface 176 of the roller electrode. Conductive portions 186 differ from the conductive portions of FIGS. 3–6 in that conductive portions 186 do not extend longitudinally along the electrode. This aspect of electrode 170 makes it conducive to a different manufacturing process than the above-embodiments.

The roller electrode 170 can be fabricated with the use of a drilling step to define the conductive portions 186. That is, holes drilled from the outer surface 176 to the bore 180 are then filled with a conductive material, such as molten metal with the use of a mandrel in the bore, to form the electrode 170. It will be appreciated that many variations to this process are possible. For example, the holes may be drilled through the diameter of the cylindrical roller and the bore drilled thereafter.

Figure 9:
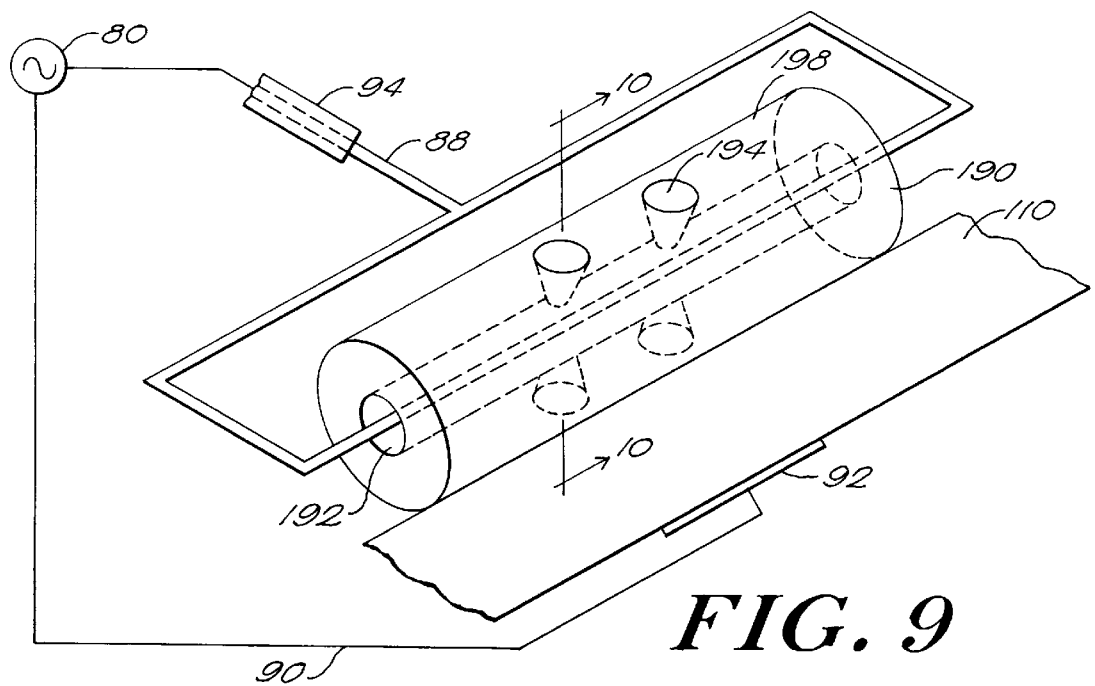
FIG. 9 is a perspective view of a segmented roller electrode according to a further alternate embodiment of the invention.
Figure 10:
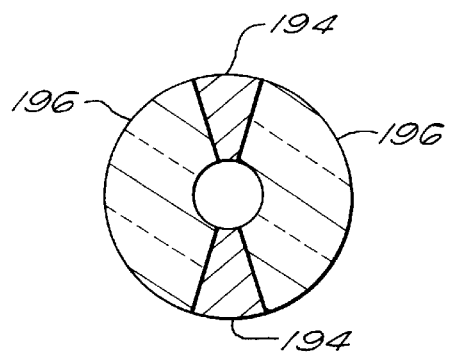
FIG. 10 is a cross-sectional view of the segmented roller electrode of FIG. 9.

As with all embodiments described herein, the size, shape and number of conductive portions 184 can be altered in order to tailor the conductive surface area on the outer surface 176 of the electrode which contacts with the tissue 110 as desired. For example, the conductive portions 186 in the embodiment of FIGS. 7 and 8 are cylindrical, or plug-shaped. Alternatively, the drilled conductive portions may be provided in a cone or pyramid-shape, as shown in FIGS. 9 and 10, in order to increase the conductive surface area of the electrode. Furthermore, two or more conductive portions 186 may be angularly spaced from one another about the circumference of the roller, as in the case of conductive portions 186a and 186b, and/or such portions may be longitudinally spaced from one another along the length of the roller, as in the case of conductive portions 186a and 186c.

Referring also to FIGS. 9 and 10, in which like numbers refer to like elements, a segmented roller electrode 190 includes conductive portions 194 and non-conductive portions 196. Electrode 190 differs from electrode 170 (FIGS. 7 and 8) in the shape of the conductive portions 194. In particular, conductive portions 194 are substantially cone-shaped, as shown. With this arrangement, the conductive surface area on the outer surface 198 of the electrode 190 is increased as compared to the conductive surface area on the outer surface 176 of electrode 170, assuming the same size and number of conductive portions are provided.

The segmented roller electrodes described above have been illustrated for use with a monopolar instrument having a return electrode suitable for remote positioning (FIG. 1) and/or an instrument having a return electrode provided as part of a sheath of the instrument body (FIG. 2). However, as mentioned above, the segmented roller electrode is likewise advantageous for use with bipolar electrosurgical instruments in order to achieve the same advantage of reduced current dissipation. FIGS. 11 and 12 illustrate exemplary bipolar segmented roller electrodes for use with a bipolar electrosurgical instrument. In these embodiments, the instrument 10 (FIG. 1) is modified to couple the return conductor 90 to the roller electrode and to eliminate the separate return pad 92. To this end, the return conductor 90, along with the active conductor 88, enters the instrument through the port 96 for coupling to the bipolar roller electrode.

Referring to FIG. 11, in which like numbers refer to like elements, the distal end 30 of the probe 26 (FIG. 1) is shown to include a bipolar segmented roller electrode 200 coupled to both the active conductor 88 covered in part by insulator 94 and return conductor 90 covered in part by an insulator 98. It is understood that other details of the distal end 30 of the probe (e.g., the inner sheath 58, the apertures 68 in the outer sheath 64, the lens 36) are omitted from FIG. 11 for simplicity of illustration. It is further understood that, as with other embodiments described herein, the extent to which the conductors 88, 90 are covered with insulation 94, 98, respectively, can be varied, for example, in the manner shown in FIG. 3.

The roller electrode 200 can be considered to include three portions: an active portion 204, an insulative disk 206 and a return portion 208, with the active and return portions spaced and electrically isolated from one another by the insulative disk. The roller electrode 200, like the other embodiments, has a substantially cylindrical shape and is adapted for rotation about a longitudinal axis X. Each of the active and return portions 204, 208, respectively, has at least one conductive portion 216 and at least one non-conductive portion 214. The conductive and non-conductive portions of the active portion 204 and return portion 208 can be provided in various arrangements, of which the embodiments of FIGS. 3–10 are illustrative. The insulative disk 206 comprises a heat stable, biologically compatible material, such as ceramics (e.g., glass, aluminum-silicate, alumina or boron), non-conductive epoxy, ceramic adhesive or other non-conductive polymers such as Teflon, Kynar and Kevlar.

Electrode 200 has a bore 210 extending along its longitudinal axis X. The active conductor 88 extends into and terminates in the bore within the active portion 204 and the return conductor 90 extends into and terminates in the bore within the return portion 208, as shown in phantom. The active and return conductors 88 and 90 are moveable relative to the respective portions 204, 208 such that the conductors 88 and 90 contact the tissue-contacting region of the respective portion and are isolated from the non-tissue-contacting region.

The illustrative bipolar electrode 200 has conductive portions 216 located on each portion 204, 208 at the same angular orientation. Thus, when the electrode 200 contacts tissue and a conductive portion of the active portion 204 contacts tissue, a conductive portion of the return portion 208 likewise contacts tissue. With this arrangement, current flows between the active portion 204 and the adjacent return portion 208 through the tissue.

Referring also to FIG. 12, in which like numbers refer to like elements, an alternate bipolar segmented roller electrode 240 is shown in contact with tissue 110. The electrode 240 is shown without the details of the distal end 30 of the probe 26 (FIG. 1) for simplicity of illustration. The bipolar segmented roller electrode 240 is coupled to the active conductor 88 covered in part by insulator 94 and return conductor 90 covered in part by insulator 98.

The electrode 240 includes conductive portions 250 and non-conductive portions 254. While the conductive portions 250 and non-conductive portions 254 are shown to be arranged in the same manner as like regions 120 and 126 of FIGS. 3 and 4, it will be appreciated that various such arrangements are suitable. Generally, the conductive portions 250 and the non-conductive portions 254 are spaced around the circumference of the roller electrode such that like portions are circumferentially opposite one another. That is, conductive portion 250a is opposite conductive portion 250b and non-conductive portion 254a is opposite non-conductive portion 254b.

The roller electrode 240 has a substantially cylindrical shape and a bore 246 extending along a longitudinal axis X about which the electrode rotates in use. In the electrode 240, both the active conductor 88 and the return conductor 90 extend through the bore 246 to contact respective regions of the electrode. More particularly, the active conductor 88 and the return conductor 90 are maintained in spaced relationship from each other in the bore 246, as shown. Preferably, conductors 88 and 90 are biased away from each other. In the illustrative embodiment, the conductors 88 and 90 are biased away from each other by a spring 260, made from an insulating material, disposed between the conductors.

With the conductors thus arranged, the active conductor 88 contacts a first region of the roller electrode, while the return conductor 90 contacts an angularly spaced region of the electrode. Specifically, the active conductor 88 contacts the tissue-contacting region of the roller electrode and the return conductor 90 contacts a non-tissue-contacting region of the electrode circumferentially opposite the tissue-contacting region, as shown.

Because conductive portions 250 are positioned circumferentially opposite other conductive portions, whenever the active conductor 88 contacts a conductive tissue-contacting region, the return conductor 90 contacts a conductive non-tissue-contacting region. Thus, current delivered to a treatment site 110 has a return path back to the energy source 80 via the isotonic fluid immediately surrounding the roller electrode and the return portion of the electrode circumferentially opposite the treatment site.

Figure 13:
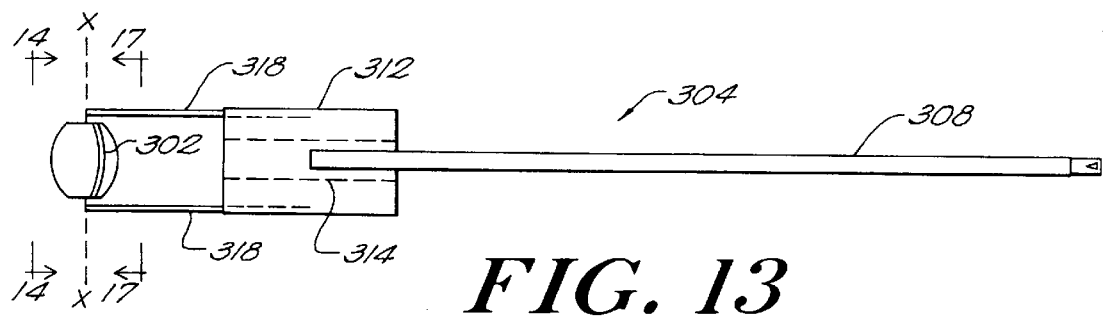
FIG. 13 is a plan view of a segmented roller electrode for use with an electrosurgical instrument according to another alternate embodiment of the invention and a portion of the electrosurgical instrument.

Referring to FIG. 13, a segmented roller electrode 300 is shown along with a portion 304 of an electrosurgical instrument of the type shown in FIG. 1 with which the electrode is used. An elongated shaft 308 is adapted for coupling to the actuator 42 (FIG. 1) which permits the electrode 300 to be retracted within the aperture 38 at the distal end 30 of the probe 26 or to extend through the aperture 38 in use and is further electrically coupled to the active conductor 88. The shaft 308 is coupled to a support 312 and, specifically, extends into a bore 314 within the support 312, as shown. Arms 318 extend from the support 312 for coupling to the roller electrode 300. More particularly, the roller electrode 300 includes a bore 348 (FIGS. 14–19) extending along a longitudinal axis X through which a conductor 320 extends. In the illustrative embodiment, the conductor 320 is a wire attached to the arms 318 by any suitable technique, such as spot welding.

The roller electrode 300 includes non-conductive portions 302 and conductive portions 306. The non-conductive portions 302 are provided by an insulative core 330 (FIGS. 14–16) and the conductive portions 306 are provided by a conductive coating 358 (FIGS. 17–19) disposed over regions of the core 330. From the outer surface 310 of the electrode 300, the arrangement of conductive and non-conductive portions is similar to that of the electrode 20 of FIGS. 3 and 4. However, as will become apparent, the roller electrodes 20 and 300 differ in cross-section and the manner in which current is delivered to the conductive portions.

Figure 14:
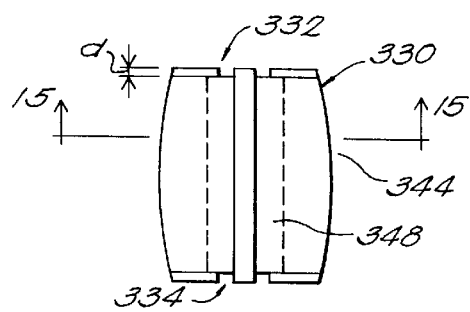
FIG. 14 is a side view of the core of the segmented roller electrode of FIG. 13 taken along line 14—14 of FIG. 13.
Figure 15:
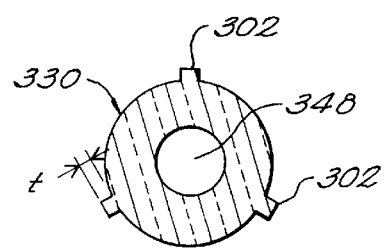
FIG. 15 is a cross-sectional view of the core of FIG. 14 taken along line 15—15 of FIG. 14.
Figure 16:
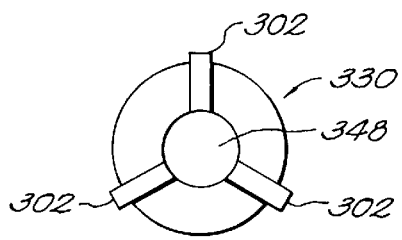
FIG. 16 is an end view of the core of FIG. 14.

Referring also to FIGS. 14, 15 and 16, the insulative core 330 of the segmented roller electrode 300 is shown during manufacture and, specifically, prior to being selectively coated. Preferably, the insulative core 330 is comprised of a ceramic and is formed by a conventional molding technique. The ceramic core 330 is substantially cylindrical in shape and includes the bore 348 extending along the longitudinal axis X between first and second ends 332, 334 of the core. Flared intermediate regions 344 may be provided between the ends 332, 334, as shown.

A plurality of protrusions extend longitudinally along the core 330, as shown, to provide non-conductive portions 302. In particular, the protrusions extend longitudinally beyond the substantially cylindrical portion of the core 330 by a relatively small distance "d" (FIG. 14), such as approximately 0.005 inches, and extend beyond the outer diameter of the cylindrical portion of the core by a relatively small distance "t" (FIG. 15), such as approximately 0.002 inches. In the illustrative embodiment, the ceramic core 330 has three protrusions angularly offset from one another around the circumference of the core 330 by approximately 120 degrees. The protrusions define the non-conductive portions 302 on the outer surface 310 of the roller electrode 300 as will become apparent.

The ceramic core 330 is selectively coated with a conductive coating material 358 to form the conductive regions 306 on the outer surface 310 of the roller electrode 300. In the illustrative embodiment, the coating is a conductive paint 358, such as a gold paint. More particularly and referring also to the views of the coated core of FIGS. 18 and 19, the coating 358 is provided along the length of the core between the non-conductive protrusions 302 with a thickness substantially equal to the distance "t". In this way, the coating "builds up" the core 330 to a diameter defined by the non-conductive protrusions 302.

Figure 17:
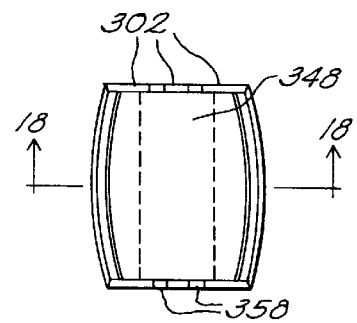
FIG. 17 is a side view of the segmented roller electrode of FIG. 13 taken along line 17—17 of FIG. 13.
Figure 18:
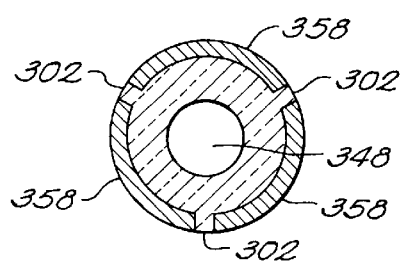
FIG. 18 is a cross-sectional view of the segmented roller electrode of FIG. 17 taken along line 18—18 of FIG. 17.
Figure 19:
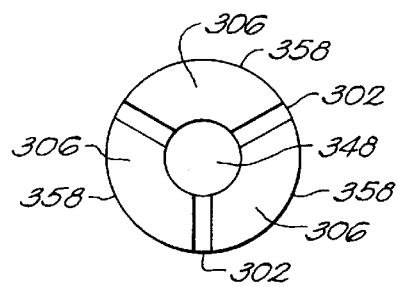
FIG. 19 is a end view of the segmented roller electrode of FIG. 13.

The ends 332 and 334 (FIG. 14) of the core 330 are also coated as shown in FIG. 19 with the conductive paint 358 to provide substantially planar end surfaces, as is apparent from FIG. 17. More particularly, the thickness of the coating on the ends of the core 330 is substantially equal to the distance "d". With this arrangement, the ends 332, 334 of the electrode have non-conductive end regions 302 spaced by conductive end regions 306, as shown in FIG. 19.

Once the conductive paint 358 is selectively deposited over the ceramic core 330, the entire electrode structure is fired in a kiln which cures both the ceramic core 330 and the conductive paint 358. This technique advantageously reduces the number of manufacturing steps by eliminating the need for separate curing steps and, further, serves to enhance the adhesion of the gold paint 358 to the ceramic core 330. It will be appreciated by those of ordinary skill in the art that the number, size and shape of the non-conductive protrusions 302 can be readily varied as desired.

Preferably, the shaft 308, support 312 and arms 318 are conductive in order to provide a mechanism for delivering current to the electrode 300. More particularly, current is delivered from the RF source 80 (FIG. 1) and the control unit 84 via the active conductor 88 (FIG. 1), the shaft 308, the support 312, the arms 318 and the wire 320. For example, each of the components 308, 312 and 318 may be comprised of stainless steel selectively coated with an insulative material.

When pressure is applied to the electrode 300 in use, the wire 320 extending through the bore 348 contacts the tissue-contacting region of the electrode 300. Thus, when the tissue-contacting region is a conductive region 306, current is delivered via the conductor 88, the shaft 308, the support 312, the arms 318, the wire 320 and the conductive end portions 306 of the electrode to the tissue-contacting region.

The foregoing description of the illustrative embodiments of the invention is presented to indicate the range of constructions to which the invention applies. Variations in the physical architecture and dimensions of the invention will be apparent to those having ordinary skill in the art based upon the disclosure herein, and such variations are considered to be within the scope of the invention in which patent rights are asserted, as set forth in the claims appended hereto. All publications and references cited herein are expressly incorporated herein by reference in their entirety.

What is claimed is:

1. An electrode assembly adapted for coupling to an energy source having an active terminal and a return terminal, the electrode assembly comprising:
a roller electrode having a substantially cylindrical shape and being rotatable about a longitudinal axis over a treatment site of a patient such that a contacting region of the roller electrode contacts the treatment site while a non-contacting region of the roller electrode is spaced from the treatment site, the roller electrode including at least one conductive portion and at least one non-conductive portion, wherein each of the at least one conductive portion corresponding to the contacting region of the roller electrode is adapted to be coupled to the active terminal of the energy source at which current is provided and each of the at least one conductive portion corresponding to the non-contacting region of the roller electrode is adapted to be isolated from the active terminal of the energy source.

2. The electrode assembly of claim 1, wherein the roller electrode has a bore extending along a longitudinal axis thereof through which a conductor adapted to be coupled to the active terminal of the energy source extends, wherein the conductor contacts the contacting region of the roller electrode.

3. The electrode assembly of claim 2, wherein each of the at least one conductive portion extends from the bore to an outer surface of the roller electrode.

4. The electrode assembly of claim 3, wherein each of the at least one conductive portion comprises a metal.

5. The electrode assembly of claim 3, wherein each of the at least one non-conductive portion comprises a material selected from the group consisting of biologically compatible ceramics and polymers.

6. The electrode assembly of claim 5, wherein each of the at least one non-conductive portion comprises an epoxy.

7. The electrode assembly of claim 3, wherein each of the at least one conductive portion extends longitudinally along at least a portion of the roller electrode.

8. The electrode assembly of claim 7, wherein each of the at least one conductive portion has a substantially pie-shaped cross-section.

9. The electrode assembly of claim 7, wherein each of the at least one conductive portion has a substantially semi-circular cross-section.

10. The electrode assembly of claim 3, wherein each of the at least one conductive portion is substantially plug-shaped.

11. The electrode assembly of claim 3, wherein each of the at least one conductive portion is substantially cone-shaped.

12. An electrosurgical instrument adapted for being energized by an energy source having an active terminal and a return terminal, comprising:
a body having a proximal portion for user handling and a distal portion; and
an electrode assembly including:
a roller electrode having a substantially cylindrical shape and being rotatable about a longitudinal axis over a treatment site of a patient such that a contacting region of the roller electrode contacts the treatment site while a non-contacting region of the roller electrode is spaced from the treatment site, the roller electrode including at least one conductive portion and at least one non-conductive portion, wherein each of the at least one conductive portion corresponding to the contacting region of the roller electrode is adapted to be coupled to the active terminal of the energy source at which current is provided and each of the at least one conductive portion corresponding to the non-contacting region of the roller electrode is adapted to be isolated from the active terminal of the energy source,
wherein the roller electrode is adapted for extending from the distal portion of the instrument body.

13. The instrument of claim 12, wherein the instrument body comprises a sheath surrounding a conductor, wherein at least a portion of the sheath is conductive and provides a return electrode adapted to be coupled to the return terminal of the energy source to which current is returned.

14. The instrument of claim 12, wherein the instrument is bipolar and each of the at least one conductive portion comprises a first conductive portion adapted to be coupled to the active terminal of the energy source and a second conductive portion isolated from the first conductive portion and adapted to be coupled to the return terminal of the energy source to which current is returned.

15. The instrument of claim 14, wherein the first and second conductive portions are angularly spaced about the circumference of the roller electrode.

16. The instrument of claim 14, wherein the first and second conductive portions are longitudinally spaced along the length of the roller electrode.

17. An electrosurgical instrument adapted for coupling to an energy source having an active terminal and a return terminal, the electrosurgical instrument comprising:

an instrument body having a proximal portion for user handling and a distal portion; and a roller electrode extending from the distal portion of the instrument body, the electrode having a substantially cylindrical shape and being rotatable about a longitudinal axis over a treatment site of a patient, the electrode having at least two conductive portions, each being separated by a non-conductive portion, wherein at least one of the conductive portions is adapted to be coupled to the active terminal of the energy source at which current is provided and at least one of the conductive portions is adapted to be isolated from the active terminal of the energy source.

18. The instrument of claim 17, wherein the roller electrode has a bore extending along the longitudinal axis and the instrument further comprises a conductor adapted to be coupled to the active terminal of the energy source and extending through the bore such that the conductor contacts the conductive portion adapted to be coupled to the active terminal.

19. The instrument of claim 18, wherein the instrument body includes a sheath surrounding the conductor, wherein at least a portion of the sheath is conductive and provides a return electrode adapted to be coupled to a return terminal of the energy source to which current is returned.

20. The instrument of claim 17, wherein the instrument is bipolar and at least one of the conductive portions is adapted to be coupled to the active terminal of the energy source and at least one of the conductive portions is adapted to be coupled to the return terminal of the energy source.

21. The instrument of claim 20, wherein the conductive portions are angularly spaced about the circumference of the roller electrode.

22. The instrument of claim 20, wherein the conductive portions are laterally spaced along the length of the roller electrode.

* * * * *